(12) United States Patent
Kumar et al.

(10) Patent No.: US 12,082,789 B2
(45) Date of Patent: *Sep. 10, 2024

(54) METHOD AND APPARATUS FOR LASER ABLATION UNDER ULTRASOUND GUIDANCE

(71) Applicant: Convergent Life Sciences, Inc., Delray Beach, FL (US)

(72) Inventors: Dinesh Kumar, Roseville, CA (US); Amit Vohra, Roseville, CA (US); Daniel S. Sperling, Boca Raton, FL (US)

(73) Assignee: Convergent Life Sciences, Inc., Delray Beach, FL (US)

(*) Notice: Subject to any disclaimer, the term of this patent is extended or adjusted under 35 U.S.C. 154(b) by 294 days.

This patent is subject to a terminal disclaimer.

(21) Appl. No.: 17/065,468

(22) Filed: Oct. 7, 2020

(65) Prior Publication Data

US 2021/0100535 A1  Apr. 8, 2021

Related U.S. Application Data

(63) Continuation of application No. 14/024,025, filed on Sep. 11, 2013, now Pat. No. 10,835,215.
(Continued)

(51) Int. Cl.
*A61B 10/02* (2006.01)
*A61B 10/00* (2006.01)
(Continued)

(52) U.S. Cl.
CPC ............ *A61B 10/02* (2013.01); *A61B 10/00* (2013.01); *A61B 10/0241* (2013.01);
(Continued)

(58) Field of Classification Search
CPC ............ A61B 34/20; A61B 2034/107; A61B 2090/378
See application file for complete search history.

(56) References Cited

U.S. PATENT DOCUMENTS

| 5,657,760 A * | 8/1997 | Ying | A61B 18/22 601/2 |
| 2010/0185087 A1* | 7/2010 | Nields | A61B 6/035 378/4 |

(Continued)

*Primary Examiner* — James M Kish
*Assistant Examiner* — Roland Dinga
(74) *Attorney, Agent, or Firm* — David I. Greenbaum; Rimon, P.C.

(57) ABSTRACT

A method for minimally invasive laser ablation of a target tissue within a patient while sparing tissue within a safety zone proximate to the target tissue, comprising: guiding a laser fiber within a patient with a guidance tool; measuring a temperature within the target tissue and the safety zone based on an invasive and a non-invasive thermal sensor; computing a thermal profile in conjunction with a real-time tissue image adapted for guidance of the laser fiber with the guidance tool within the patient; and controlling a laser to deliver energy through the laser fiber, to deliver a minimally therapeutic ablation therapy to the target tissue while ensuring that the safety zone is maintained in a non-ablation condition, based on at least a treatment plan, the measured temperature, and the thermal profile.

34 Claims, 4 Drawing Sheets

Related U.S. Application Data

(60) Provisional application No. 61/700,273, filed on Sep. 12, 2012.

(51) Int. Cl.
*A61B 18/20* (2006.01)
*A61B 34/10* (2016.01)
*A61B 34/20* (2016.01)
*A61B 90/00* (2016.01)
*A61B 17/00* (2006.01)

(52) U.S. Cl.
CPC .............. *A61B 18/20* (2013.01); *A61B 34/10* (2016.02); *A61B 34/20* (2016.02); *A61B 90/361* (2016.02); *A61B 90/39* (2016.02); A61B 2017/00274 (2013.01); A61B 2034/107 (2016.02); A61B 2090/364 (2016.02); A61B 2090/365 (2016.02); A61B 2090/378 (2016.02)

(56) References Cited

U.S. PATENT DOCUMENTS

| | | | | |
|---|---|---|---|---|
| 2011/0087096 | A1* | 4/2011 | Behar | A61B 8/48 |
| | | | | 600/549 |
| 2013/0231567 | A1* | 9/2013 | Barthe | A61B 8/4245 |
| | | | | 600/459 |

* cited by examiner

METHOD AND APPARATUS FOR LASER ABLATION UNDER ULTRASOUND GUIDANCE

CROSS REFERENCE TO RELATED APPLICATIONS

The present application is a continuation of U.S. Non-Provisional patent application Ser. No. 14/024,025, filed Sep. 11, 2013, now U.S. Pat. No. 10,835,215 entitled "METHODS AND APPARATUS FOR LASER ABLATION UNDER ULTRASOUND GUIDANCE," which claims priority to U.S. Provisional Patent Application No. 61/700,273, filed Sep. 12, 2012. The contents and disclosures of the above applications are incorporated herein by reference in their entireties for all purposes.

BACKGROUND OF THE INVENTION

Field of the Invention

The present disclosure relates to systems and methods for image guided laser ablation procedures.

Description of the Art

Previous Art

A large number of medical procedures involve local tissue ablation in order to treat a condition or ablate a malignancy. For example, tissue ablation can be used to treat a benign condition called benign prostate hyperplasia (BPH), as well as a malignant condition such as prostate cancer. Thermal ablation methods find widespread applications in such medical procedures where both cooling and heating methods are involved. Cryotherapy ablates the tissue by cooling it down to a temperature where the cell necrosis occurs while laser therapy performs cell necrosis by raising temperature to unsafe limits for the tissue being ablated. When trying to localize the ablation, cryotherapy suffers from the disadvantage that the temperature gradient is very large from the body temperature to the ablation temperature. The tissue has to be locally cooled down to around −40° C. to ablate, which results in temperature gradient of 77° C. compared to body temperature. As a result, while the tissue is being locally cooled, the surrounding tissue is also cooled down to very unsafe temperatures. The ablation is thus hard to control and causes irreparable damage to healthy tissue.

Tissue ablation through heating does not suffer from this drawback since the temperature only needs to be raised from 37° C. to about 60° C. As a result, the ablation zone can be contained to small regions while limiting the damage to surrounding structures. Laser ablation provides one such method where localized heat can be provided to a target within an organ, gland or soft tissue such that the target area can be completely and reliably ablated while preserving important surrounding structures. Further, laser pulses can provide large amounts of energy over short periods, thus increasing the achievable peak thermal gradients. Laser energy is typically applied to the internal tissues and structures using a hypodermic needle sleeve. The needle is inserted into the target and a fiber, through which laser energy is applied, is inserted through the needle to place it at the target. The laser source is then activated and the delivered thermal energy ablates tissue within the ablation zone. The traditional drawback to using laser ablation is that it cannot be performed under ultrasound guidance since traditional ultrasound systems and methods do not provide thermometry information. That is, while ultrasound can localize the laser fiber within the target tissue, it cannot provide feedback of the temperature of the tissue, and therefore the ablation effect. One compromise has been to observe temperature of ablation using MR thermometry. However, this method is cumbersome, very expensive, and requires prolonged access to MR gantry, which makes it an unfeasible procedure for a vast majority of surgeons. In addition, the learning curve to perform a laser ablation in MR gantry can be very steep. See, U.S. Pat. Nos. 8,498,461; 8,496,587; 8,482,285; 8,480,600; 8,478,380; 8,439,907; 8,427,154; 8,425,424; 8,417,316; 8,409,099; 8,401,614; 8,369,930; 8,368,401; RE 43,901; 8,326,010; 8,319,495; 8,311,641; 8,278,053; 8,277,379; 8,251,908; 8,235,901; 8,216,161; 8,187,270; 8,088,067; 8,057,391; 8,052,604; 8,030,922; 8,002,706; 7,949,384; 7,792,566; 7,772,846; 7,771,418; 7,635,722; 7,508,205; 7,426,409; 7,422,568; 7,359,745; 7,358,729; 7,084,626; 7,078,903; 6,823,216; 6,763,261; 6,615,071; 6,589,174; 6,559,644; 6,542,767; 5,753,207; 4,951,688; 5,792,070; 6,419,635; 6,500,121; 6,575,969; 6,589,174; 6,916,290; 7,367,944; 7,799,019; 8,012,148; 8,016,757; 8,226,559; 2002/0099304; 2006/0259024; 2009/0182230, expressly incorporated herein by reference.

U.S. Pat. No. 7,699,838, expressly incorporated herein by reference, entitled "System and methods for image-guided thermal treatment of tissue", relates to a system and methods for modeling the death of tissue cells that are thermally treated using thermal treatment devices is disclosed. A cell-death model seeks to accurately predict, in real-time, which voxels of cells are dead or are about to die as the thermal treatment is applied to these cells. The effects of thermal treatment are monitored by a thermal measurement device which feeds thermal information to the cell-death model. The cell-death model seeks to account for the temperature of each voxel of tissue cells with respect to a temperature threshold value and the duration over which the thermal treatment is applied. When the thermal measurement device is an imaging device, the results of the thermal treatment may be displayed to the user in real-time. As a result, a user of the thermal treatment device can determine, in real-time, which target voxels of cells he has killed and which still need to be killed. The user can also more easily avoid inadvertently killing healthy tissue that he does not intend to kill. The cell-death model may be implemented in software on the thermal measurement device, on the thermal treatment device, or on a separate processing device which interfaces to and communicates with at least one of the thermal measurement device and the thermal treatment device.

U.S. Pat. No. 5,109,859, expressly incorporated herein by reference, entitled "Ultrasound guided laser angioplasty", discloses a laser ablation catheter system guided by ultrasound sonography particularly useful for removing atherosclerotic plaque from coronary arteries of patients with heart disease. Ultrasound is employed at the tip of the catheter to determine where the plaque is with reference to the arterial wall. After a sonographic image is made, an ablative laser element is aimed at the plaque to ablatively remove the plaque under computer guidance. In one embodiment, the laser is able to fire in a forward direction after first determining the laser's path to be intraluminal in order to create or recanalize a central channel. In another embodiment, the laser is able to fire circumferentially at the arterial wall guided as to depth and direction by the ultrasound computer interface. Both functions may be provided in one laser angioplasty catheter system. The system also includes manual and computer safety overrides. See also, U.S. Pat. Nos. 5,366,490; 5,370,675; 5,385,544; 5,409,453; 5,421,819; 5,435,805; 5,456,662; 5,470,308; 5,470,309; 5,514,131; 5,531,677; 5,542,915; 5,554,110; 5,556,377; 5,582,171; 5,599,294; 5,599,295; 5,607,389; 5,630,794; 5,672,153; 5,720,718; 5,720,719; 5,769,812; 5,769,843; 5,792,094; 5,848,986; 5,849,005; 5,853,368; 5,885,238; 5,895,370; 5,935,075; 5,944,687; 5,967,984; 6,013,072; 6,022,309; 6,022,334; 6,033,371; 6,047,216; 6,102,886; 6,149,596; 6,199,554; 6,206,847; 6,309,382; 6,368,318; 6,379,325; 6,406,486; 6,436,059; 6,464,661; 6,475,159; 6,514,249; 6,546,276; 6,615,071; 6,645,197; 6,651,672; 6,669,686; 6,763,261; 6,863,653; 6,869,429; 6,972,015; 6,993,382; 6,997,924; 7,123,968; 7,156,816; 7,201,731; 7,201,749; 7,291,146; 7,344,528; 7,426,409; 7,477,925; 7,513,876; 7,603,166; 7,742,795; 7,935,108; 8,007,440; 8,025,661; 8,152,795; 8,187,621; 8,231,613; 8,241,272; 8,267,932; 8,277,444; 8,333,758; 8,364,237; 8,366,705; 8,383,158; 8,396,548; 8,401,667; 8,444,639; 8,480,593; 8,496,653, each of which is expressly incorporated herein by reference.

U.S. Pat. No. 8,155,416, expressly incorporated herein by reference, entitled "Methods and apparatuses for planning, performing, monitoring and assessing thermal ablation," discloses a thermal ablation system using an x-ray system to measure temperature changes throughout a volume of interest in a patient. Image data sets captured by the x-ray system during a thermal ablation procedure provide temperature change information for the volume being subjected to the thermal ablation. See also, U.S. Pat. No. 7,871,406, expressly incorporated herein by reference.

U.S. Pat. No. 7,172,757, expressly incorporated herein by reference, entitled "Methods and devices for image-guided manipulation or sensing or anatomic structures", discloses devices and methods for identifying or observing a precise location in the body through and/or upon which medical procedures such as laser ablation may be efficiently and safely performed. The methods disclosed in the patent application use image guidance with ultrasound or optical coherence tomography imaging without computation or display of thermal maps/thermal measurements or tracking methods.

U.S. Pat. No. 6,669,693, expressly incorporated herein by reference, entitled "Tissue ablation device and methods of using," discloses a tissue ablating device and the method of using radiofrequency signal and monitoring with ultrasound or intra cardiac echo device for treating cardiac arrhythmias. The patent has no claims on providing thermal measurements, thermal maps or overlays with other imaging modalities. The method claimed does not provide for any control of ablation sources or use of a guidance tool or tracking method to localize the tissue ablation.

U.S. Pat. No. 8,137,340, expressly incorporated herein by reference, entitled "Apparatus and method for soft tissue ablation employing high power diode-pumped laser," and U.S. Pat. No. 7,313,155, expressly incorporated herein by reference, entitled "High power Q-switched laser for soft tissue ablation," disclose laser ablation with a high power diode-pumped laser and high power Q-switched solid-state laser respectively for ablating soft tissue with laser.

See also, U.S. Pat. Nos. 5,109,859; 5,451,221; 5,476,461; 5,498,258; 5,545,195; 5,630,837; 5,657,760; 5,700,260; 6,024,703; 6,056,742; 6,203,524; 6,228,049; 6,325,792; 6,375,634; 6,387,088; 6,428,532; 6,436,059; 6,440,127; 6,447,477; 6,459,925; 6,494,844; 6,517,534; 6,546,276; 6,642,274; 6,692,493; 6,743,226; 6,751,490; 6,863,653; 6,869,429; 6,942,657; 6,945,942; 7,015,253; 7,044,964; 7,496,398; 7,621,889; 7,621,890; 7,623,625; 7,627,085; 7,632,262; 7,644,715; 7,711,089; 7,724,871; 8,123,729; 8,287,602; 8,361,066; 8,365,741; 8,377,032; 8,435,233; RE. 42,049, each of which is expressly incorporated herein by reference.

See also, US Pub. Pat. App. 20130211230; 20130023714; 20130018260; 20110190662; 20110104052; 20100331814; 20100317960; 20100298622; 20100292766; 20100179652; 20100092424; 20100030203; 20100016846; 20090216261; 20090156977; 20090143674; 20080146912; 20080071333; 20070225544; 20070149878; 20070005050; 20060282039; 20060142789; 20060015085; 20050033315; 20040054268; 20030073895; 20020072673, each of which is expressly incorporated herein by reference.

See also, Gillams, Alison R., Lees, William R., "Survival after percutaneous, image-guided, thermal ablation of hepatic metastases from colorectal cancer", J Diseases of the Colon & Rectum, V 43, N 5, P 656-661 (2000); Claudio M. Pacella, MD, Giancarlo Bizzarri, MD, Rinaldo Guglielmi, MD, Vincenzo Anelli, MD, Antonio Bianchini, MD, Anna Crescenzi, MD, Sara Pacella, MD and Enrico Papini, MD. "Thyroid Tissue: US-guided Percutaneous Interstitial Laser Ablation—A Feasibility Study", December 2000 Radiology, 217, 673-677; Papini E, Bizzarri G, Bianchini A, Valle D, Misischi I, Guglielmi R, Salvatori M, Solbiati L, Crescenzi A, Pacella C M, Gharib H., "Percutaneous Ultrasound-Guided Laser Ablation Is Effective for Treating Selected Nodal Metastases in Papillary Thyroid Cancer", J. Clin. Endocrinol. Metab. Jan. 1, 2013 98:1 E92-E97; Feng B, Liang P, Cheng Z, Yu X, Yu J, Han Z, Liu F., "Ultrasound-guided percutaneous microwave ablation of benign thyroid nodules: experimental and clinical studies" Eur J Endocrinol Jun. 1, 2012 166:6 1031-1037; DØssing H, Bennedbaek F N, Hegedüs L., "Effect of ultrasound-guided interstitial laser photocoagulation on benign solitary solid cold thyroid nodules—a randomised study", Eur J Endocrinol Mar. 1, 2005 152:3 341-345; Pacella C M, Bizzarri G, Spiezia S, Bianchini A, Guglielmi R, Crescenzi A, Pacella S, Toscano V, Papini E., "Thyroid Tissue: US-guided Percutaneous Laser Thermal Ablation", Radiology Jul. 1, 2004 232:1 272-280; DØssing H, Bennedbaek F N, Karstrup S, HegedüL., "Benign Solitary Solid Cold Thyroid Nodules: US-guided Interstitial Laser Photocoagulation—Initial Experience", Radiology Oct. 1, 2002 225:1 53-57; Bennedbaek F N, Karstrup S, Hegedüs L., "Ultrasound guided laser ablation of a parathyroid adenoma", Br. J. Radiol. Oct. 1, 2001 74:886 905-907; and Papini E, Guglielmi R, Bizzarri G, Pacella C M., "Ultrasound-Guided Laser Thermal Ablation For Treatment Of Benign Thyroid Nodules", Journal Endocrine Practice, Volume 10, Number 3/May/June 2004, 1934-2403 (Online), Pages 276-283, each of which is expressly incorporated herein by reference.

Consequently, there exists a need for improved systems and methods for performing for image-guided laser ablation procedures.

SUMMARY

The present technology provides a system and method for employing ultrasound guidance of tissue ablation, which employs multiple thermal sensors placed within the tissue at the time of treatment to provide real-time feedback of spatial thermal profile. Preferably, the feedback directly measures the temperature of tissue to be ablated, and tissue to be spared, though an array of thermal sensors may be provided which provide other temperatures. Likewise, a thermal sensing array may be used to estimate a temperature at a location within or near the target, even if that temperature is not directly measured. The technology is preferably minimally invasive, and thus preferably does not require or employ a surgical incision to directly expose the tissue to be treated. Rather, the treatment is provided without substantially disrupting surrounding tissues or organs, though piercing such surrounding tissues with needles is contemplated within the scope of the therapy.

The apparatus for performing the method of minimally-invasive image-guided laser ablation of targeted region within a tissue or organ comprises a guidance tool configured to guide a laser source to a predefined target region from a planning image, a controller configured to control energy from the laser source, a duration of its application, and dosage of energy from the laser source, and at least one automated processor, e.g., a computer with software that can compute thermometry based on precise location and duration of application or dosage of the laser source. The controller receives signals from the at least one automated processor for control or shut-off of the laser energy, to selectively ablate tissue to be destroyed, and to preserve other tissues. The guidance tool may use, for example, magnetic, optical, mechanical or co-registration software based tracking. In some embodiments, the controller and the automated processor may be integrated.

The tissue or organ to be treated may be prostate, heart, lung, kidney, liver, bladder, ovaries, thyroid, or brain, or other tissues in man or animal. Similarly, the technology may be applied to non-animal targets. The target region to be ablated may be a malignant (cancerous) or benign (non-cancerous) condition.

The target region to be ablated may be a portion or the entire volume of the target tissue/organ. Where part of a tissue or organ is not intended to be ablated, preferably it is spared, for example maintained within a safe thermal range to avoid substantial and persistent loss of function. Within an organ, there may be an intermediate or transitional zone, where partial loss of function or persistent effect is present, but without immediate necrosis. In this case, it is preferred that the at least one automated processor define a therapeutic envelope to ensure that all tissue intended to be ablated is sufficiently treated, that tissues to be preserved are not ablated, and critical functions of tissues outside of the ablation zone are preserved. Thus, in defining the therapy, a part of a tissue or surrounding structure may be identified as a sensitive region that must be spared from damaging delivery of energy, and the system controlled within that constraint.

According to one embodiment, the therapy is provided by a laser fiber inserted through a hypodermic needle. The part of tissue or surrounding structure may be identified as the region to be avoided while inserting a hypodermic needle, for example under ultrasonic guidance of the needle insertion.

Thermal sensors may be inserted at various locations around the laser source to measure temperature at various distances from the laser source. The temperature measurements may be displayed on a display screen, such as a cathode ray tube, liquid crystal display monitor, plasma display monitor, heads-up display, 3D display, projection display, Google Glass™ or other integrated eyewear display system. Haptic feedback may also be incorporated, especially where the laser fiber is manually or semi-automatically advanced by a surgeon during the procedure. The automated processor(s) may employ as part of their control algorithm the thermal map as displayed, or may employ a different representation of the tissue temperatures and/or predictive model of the effect of the laser energy on future thermal conditions within the target tissue.

The thermal sensors may be hypodermic needles or surface sensors, or combination of them. In some cases, optic fibers may be used to measure tissue temperatures, and indeed the same optic fiber used to deliver the ablative energy may also measure the tissue temperature at the tip.

The automated processor may be configured to compute the tissue temperatures (thermometry) using ultrasound thermometry techniques, such that the live (real time) ultrasound is analyzed for computing temperature within its field of view. See, U.S. Pat. Nos. 8,517,962; 8,512,262; 8,480,585; 8,469,904; 8,460,193; 8,409,097; 8,374,674; 8,295,912; 8,256,953 (and cited references); U.S. Pat. Nos. 8,235,909; 8,166,332; 7,726,875; 7,699,838 (and Breen et al, "MRI-guided Laser Thermal Ablation: Model to Predict Cell Death from MR Thermometry Images for Real-time Therapy Monitoring", Sep. 1-5, 2004, IEEE, 1028-1031); U.S. Pat. Nos. 7,740,056; 7,229,411; 6,542,767; 6,500,121; and 6,050,943, each of which, along with their respective cited references, are expressly incorporated herein by reference in their entirety.

The automated processor may execute software which computes thermometry using heat equations. The duration of application and energy delivered by the laser source constitute the parameters for computing the thermal map.

A combination of hypodermic and surface thermal sensor measurements, ultrasound signal analysis and heat equations may be analyzed together to provide an accurate temperature measurement for regions within the tissue.

The therapy may be performed by guiding one or more laser source(s) under guidance of a live B-mode ultrasound image. Alternately, or in addition, two orthogonal planes of ultrasound can be simultaneously captured and used for guidance. Further, live 3D ultrasound images may be used for guidance of the laser fiber tip.

According to one embodiment, software executing on the automated processor can display a thermal map as either colored overlay or isothermal contours. The isothermal contours preferably include displaying the isocontours at temperatures of $T_{safety}^{high}$ and $T_{ablation}^{low}$, where $T_{safety}^{high}$ represents the highest temperature allowable within safety zone and $T_{ablation}^{low}$ represents the lowest temperature needed in the ablation zone to ensure complete ablation. The safety zone represents the region that must be spared during the procedure. The software may display a thermal map overlay as either a colored overlay or isothermal contours onto a live ultrasound image.

In a specific embodiment, the thermal sensors are inserted in a grid-like pattern using an external physical grid with holes at grid points to allow insertion of needles, with the needle tips inserted into the tissue in an array, with the tips either in a predetermined pattern, or the position of the tips measured using an imaging technology such as ultrasound, X-ray, CT scan, MRI, or the like. The needles may be associated with thermal sensors, such that a temperature at a tip of each needle may be acquired and recorded, or associated with laser sources, or in some cases, both. A virtual grid may be displayed that is consistent with the physical grid, such that each grid point location in the virtual grid matches with a corresponding grid location in the tissue. Upon identification of the grid locations containing the laser source, the thermal map may be computed and displayed as an overlay on the virtual grid, either as a color coded map or as isothermal contour overlays.

The virtual grid and thermal maps may be displayed as an overlay on live ultrasound images. In one embodiment, the needle may be automatically detected in ultrasound images as it is advanced to or through a target location.

Some points on the display may be selected for specific temperature measurements such that an ablation zone can be defined where temperature exceeds a pre-defined threshold. Likewise, some points on the display may be selected or pre-defined for specific temperature measurements such that a safety zone can be defined where the temperature should not exceed a pre-defined threshold. If the temperature exceeds the threshold at those regions, the apparatus sounds an alarm or automatically shuts off.

In one embodiment, a laser source is inserted through a grid, which has a corresponding virtual grid. This may be identified on the virtual grid by selection of one or more grid points as the sources.

In one specific embodiment for prostate ablation, a transperineal grid with a matrix of holes is attached to, and calibrated to the ultrasound probe, such that the ultrasound video image has a known rigid correspondence with the virtual grid. In this embodiment, one or more hollow needles are advanced through the holes in the transperineal grid so that laser fiber can be inserted within a hollow needle to a target region for ablation. Hypodermic thermal sensors are then advanced through different needles to locations in the grid, such that some sensors are placed close to the ablation zone to confirm ablation while some other sensors are placed close to safety zone to avoid reaching threshold temperatures.

In one embodiment, the target region and laser fiber placements are planned using a planning image acquired before a procedure. The planning image may be through a different modality, such as CT scan, PET, MRI, MSRI, or the like. The software loads this plan and maps it to a frame of reference of the live ultrasound image, which may involve a coordinate transformation and/or a deformation of the tissues to account for deviations from linear geometry, especially for ultrasound images. The needle for laser guidance is then placed according to the plan through the transperineal grid. The plan for each needle is represented by $\{(i,j)_k, D_k, t_k\}$ where $(i,j)_k$ represents the grid location, $D_k$ and $t_k$ represent the depth of insertion and duration of laser application respectively, for the k-th laser source.

According to a different embodiment, the needle placement is performed transperineally using a guidance tool that allows for inclined needle guidance.

In another embodiment invention, the needle placement is performed transrectally without use of an external grid. The embodiment comprises the following: a hardware device mounted on the transrectal needle guide that allows insertion of multiple needles for placement of laser fibers and hypodermic thermal sensors; and a rectal surface thermal sensor that is placed on the rectum wall transrectally. The thermal sensor may be attached to the ultrasound transducer.

A plan may be defined based on information from other medical imaging modalities, such as one or more of PET, CT, MRI, MRSI, Ultrasound, Echo Cardiograms and Elastography, which can be combined with a live B-mode ultrasound image or two orthogonal planes of simultaneously captured ultrasound images, or a live 3D ultrasound image, to provide guidance to one or more laser source(s). The information obtained by various imaging modalities may be combined using computerized or cognitive image co-registration. The computerized or cognitive image co-registration may utilize external markers or fiducials for initial registration. The computerized co-registration may also be achieved using rigid registration, affine registration, elastic registration, or a combination of these mentioned registration methods.

It is therefore an object to provide a system for performing minimally invasive laser ablation of a target tissue within a patient while sparing tissue within a safety zone proximate to the target tissue, comprising: a guidance tool configured to guide a laser fiber within a patient; a controller configured to control a laser to deliver energy through the laser fiber; and at least one automated processor configured to at least measure a temperature within the target tissue and the safety zone, for example based on both an invasive thermal sensor and a non-invasive thermal sensor, to control the controller to deliver a minimally therapeutic ablation therapy to the target tissue based on at least a treatment plan, while ensuring that the safety zone is maintained in a non-ablation condition. The at least one processor may compute a thermal profile in conjunction with a real-time tissue image adapted for guidance of the laser fiber with the guidance tool within the patient. The safety zone is preferably continually maintained below an ablation temperature, though in some cases the time-average or biological effect of the laser is computer, rather than a strict thermal limit.

The guidance tool may be configured to automatically control insertion of the laser fiber into the patient. The guidance tool may also be configured to guide the invasive thermal sensor within the patient. The guidance tool may employ at least one of magnetic, optical, mechanical and co-registration software-based tracking. The guidance tool may be configured to guide the invasive thermal sensor into the safety zone. The guidance tool may comprise a perforated plate having a regular array of holes configured to guide the laser fiber. The guidance tool may comprise a perforated plate having a regular array of holes configured to guide the invasive thermal sensor. The guidance tool may be mounted to an ultrasonic transducer for generating a real-time ultrasound image, and have an array of guided trajectories which define one at least one plane of a virtual grid and which are configured to guide the laser fiber along a respective guided trajectory, and wherein the at least one automated processor is configured to generate a thermal map which is overlaid on the real-time ultrasound image.

The controller may be further configured to define a duration and dosage of laser energy delivered through the laser fiber. The non-invasive thermal sensor may comprise an ultrasound thermometer.

The ultrasound thermometer may generate the real-time image of at least the target tissue during ablation. The invasive and the non-invasive thermal sensor may comprise a combination of a hypodermic thermal sensor, a surface thermal sensor, and an ultrasound signal analysis thermal sensor, which are together analyzed by the at least one automated processor to provide an accurate temperature measurement.

The at least one automated processor may be configured to communicate with the controller to deactivate the delivery of laser energy through the laser fiber based on the computed thermal profile. The at least one automated processor may also be configured to execute software to compute the thermal profile using heat equations, based on at least a duration of application and an energy delivered by the laser fiber, to create a thermal map.

The treatment plan may be based on an imaging modality having a first correspondence to a physical coordinate system, and the minimally invasive laser ablation is conducted using a real-time tissue imager have a second correspondence to the physical coordinate system, the first and second correspondences being different, wherein the at least one automated processor is configured to perform an image transform such that the treatment plan corresponds to an image derived from the real-time tissue imager. The first imaging modality may be selected from at least one of PET, CT, MRI, and MRSI, and the real-time tissue imager may be an ultrasonic imager, e.g., B scan, orthogonal axis, 3D, etc.

It is another object to provide a method for minimally invasive laser ablation of a target tissue within a patient while sparing tissue within a safety zone proximate to the target tissue, comprising: guiding a laser fiber within a patient with a guidance tool; measuring a temperature within the target tissue and the safety zone based on an invasive and a non-invasive thermal sensor; computing a thermal profile in conjunction with a real-time tissue image adapted for guidance of the laser fiber with the guidance tool within the patient; and controlling a laser to deliver energy through the laser fiber, to deliver a minimally therapeutic ablation therapy to the target tissue while ensuring that the safety zone is maintained in a non-ablation condition, based on at least a treatment plan, the measured temperature, and the thermal profile.

The guidance tool may automatically control insertion of the laser fiber into the patient, and manually or automatically guide insertion of the invasive thermal sensor into the tissue. Preferably, an invasive thermal sensor is guided into the safety zone, to directly measure the temperature. The guidance tool may comprise a perforated plate having a regular array of holes configured to guide the laser fiber and the invasive thermal sensor.

The method may further comprise controlling a duration and a dosage of laser energy delivered through the laser fiber. Further, the method may comprise deactivating the delivery of laser energy through the laser fiber based on at least the computed thermal profile.

The non-invasive thermal sensor comprises an ultrasound thermometer and/or a surface thermal sensor. The invasive thermal sensor may comprise a thermocouple, a thermistor, a temperature sensing semiconductor junction, a fiber optic temperature probe, or other thermal sensor, preferably adapted to fit within a hypodermic needle, i.e., a 12 Ga. needle. The invasive and the non-invasive thermal sensor may comprise a combination of a hypodermic thermal sensor, a surface thermal sensor, and an ultrasound signal analysis thermal sensor, which are together analyzed to provide an accurate temperature measurement. The guidance tool may be mounted to an ultrasonic transducer for generating a real-time ultrasound image, and has an array of guided trajectories which define one at least one plane of a virtual grid and which guide the laser fiber along a respective guided trajectory, and wherein a thermal map is generated and overlaid on the real-time ultrasound image.

According to one embodiment, the same ultrasound transducer that senses tissue temperature may also generate an ultrasound real-time image of at least the target tissue during ablation.

The thermal profile may be computed using heat equations, based on at least a duration of application and an energy delivered by the laser fiber.

The treatment plan may be based on an imaging modality having a first correspondence to a physical coordinate system, and the minimally invasive laser ablation is conducted using a second imaging modality have a second correspondence to the physical coordinate system, the first and second correspondences being different, further comprising performing an image transform such that the treatment plan corresponds to an image derived from the second imaging modality. The image transform may correct for distortions, tissue elasticity and deformation, organ displacement, and the like. The first imaging modality may be selected from at least one of PET, CT, MRI, and MRSI. The second imaging modality may ultrasound imaging, e.g., B-mode, two orthogonal planes of ultrasound, or a 3D ultrasound image.

The target tissue may comprise prostate, heart, lung, kidney, liver, bladder, ovaries, thyroid, or brain. The target tissue may represent a tumor, e.g., benign or malignant, an inflammation or hypertrophy, or other pathology.

A thermal map may be displayed as a set of isothermal regions overlaid on the real-time image, representing at least $T_{safety}^{high}$, $T_{ablation}^{low}$, and $T_{safety}^{low}$ which represent the highest temperature allowable within safety zone, the lowest temperature needed in the ablation zone to ensure complete ablation, and the temperature of the safety zone at which the laser can be reactivated.

A further object provides a non-transitory computer readable medium which stores computer readable instructions to control a programmable processor, for support of minimally invasive laser ablation of a target tissue within a patient while sparing tissue within a safety zone proximate to the target tissue, to perform the steps of: receiving data representing at least one temperature within a target tissue and the safety zone based on information from at least one invasive thermal sensor and at least one non-invasive thermal sensor; computing a thermal profile of the target tissue and the safety zone in conjunction with a real-time tissue image adapted for guidance of a laser fiber toward the target tissue; and controlling a laser to deliver energy through the laser fiber, to deliver a minimally therapeutic ablation therapy to the target tissue while ensuring that the safety zone is continually maintained in a non-ablation condition, based on at least a treatment plan, the measured temperature, and the thermal profile.

DESCRIPTION OF THE EMBODIMENTS

The present technology provides systems and methods for performing targeted laser ablation as part of a medical procedure. The target of the ablation procedure may include a malignancy or benign inflammation. Specifically, the apparatus may include three components: a guidance tool for guiding a source of laser energy, such as a fiber optic, to or near a target region; an ablation controller for controlling delivery of the laser energy; and an automated subsystem that computes and displays temperature measurements of the target and certain surrounding or nearby areas, and which provides control signals to the ablation controller. The ablation controller and the automated subsystem may be integrated. See, e.g., U.S. Pat. No. 8,506,485, and cited references, expressly incorporated herein by reference.

The guidance tool used for placing the source of laser energy near the target tissue may contain a tracking device, such that after an initial calibration with an external coordinate system, I.e., the "real world", the tracking device can be manipulated to align a needle with the desired target within the tissue. The tracking tool provides a trajectory for aligning the needle, which is manually or automatically inserted along the trajectory.

The ablation controller provides the interface between the automated subsystem, e.g., computer, and the source of laser energy, which is, for example, a fiber optic laser source. The computer computes and monitors the temperature, and in case of a software based tracking system, the trajectory of the needle. The computer provides feedback to the ablation controller to start or stop laser energy delivery. In addition, the computer is equipped with a display monitor that provides visual feedback of both physical location of the therapy and thermography to the user.

Figure 1:
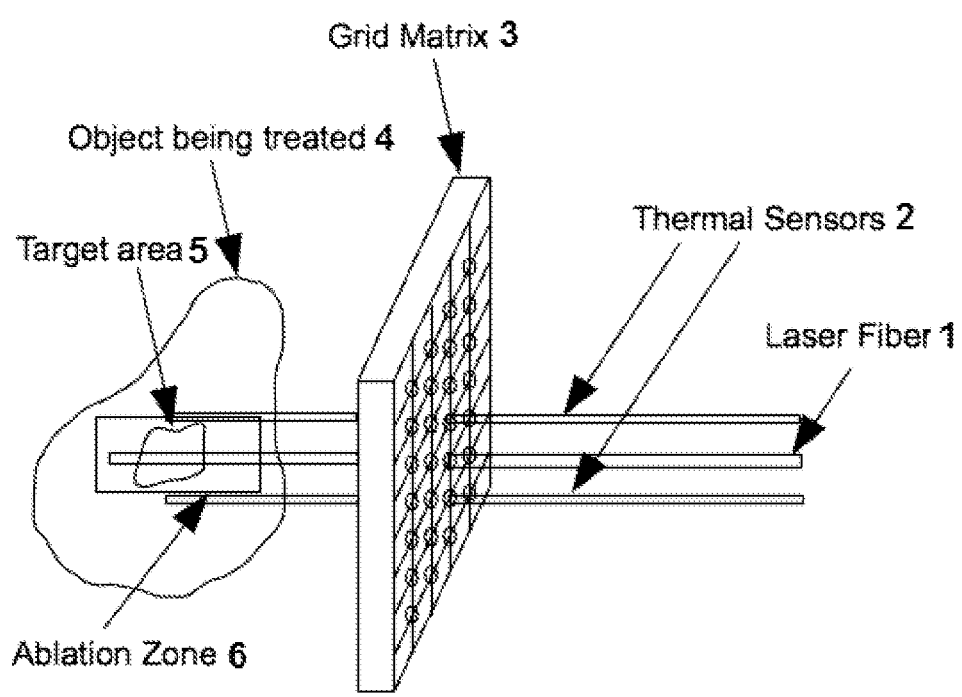
FIG. 1 shows a schematic drawing of a grid matrix template for positioning a laser fiber and thermal sensors into or near an object to be treated.
Figure 2:
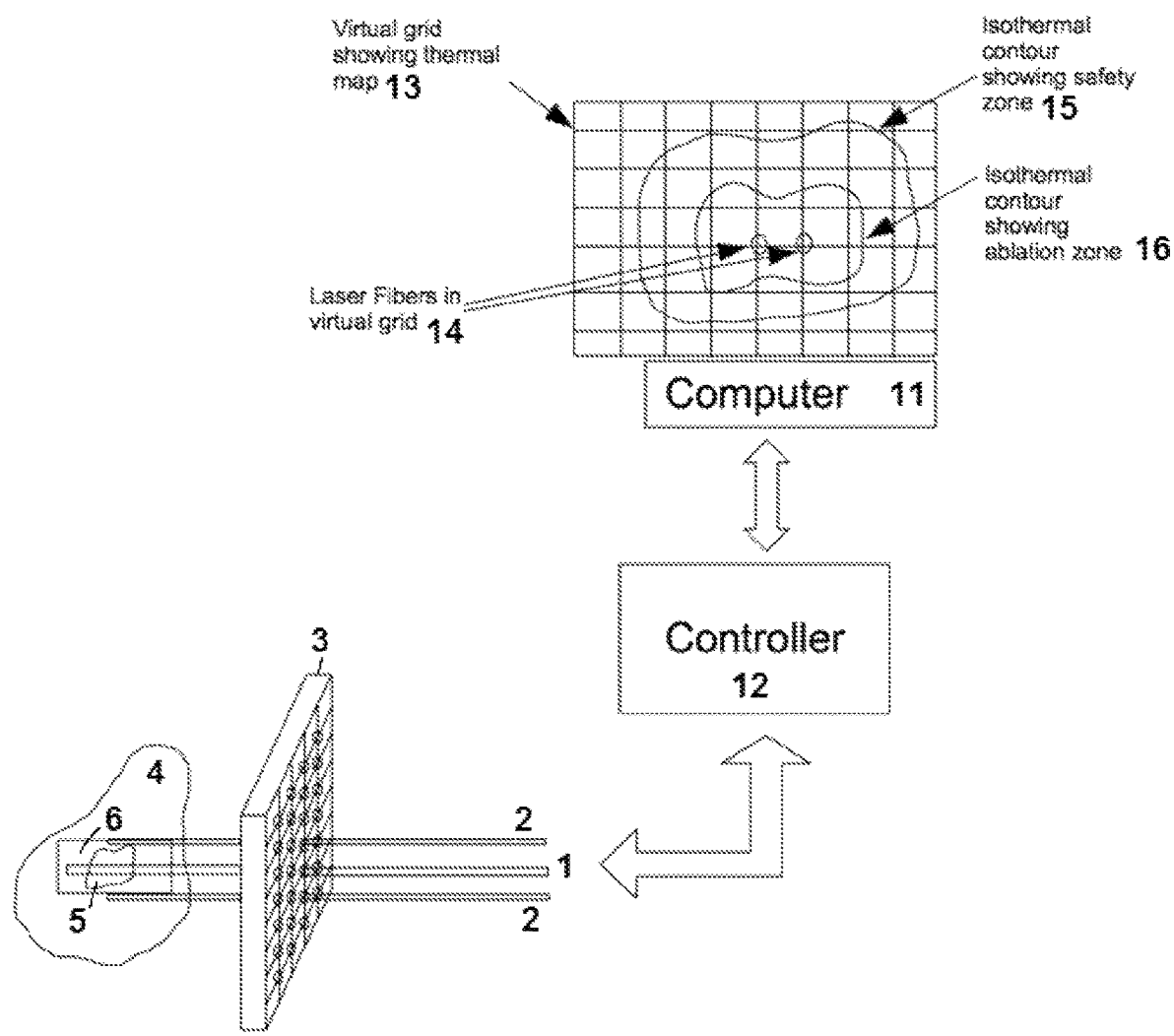
FIG. 2 shows a schematic drawing of showing laser ablation using the grid template and thermometry feedback to a controller and to a user through a display.

FIGS. 1 and 2 show one particular embodiment in detail where a brachytherapy-like grid matrix 3 is used to guide needles. Note that the methodology does not change even if a tracking system is used for guiding various needles to their targets. As shown in FIG. 1, the apparatus includes a grid 3, which has pinholes at various grid locations. Each pinhole location may be individually identified. For example, if the rows are labeled as 1, 2, 3, . . . and the columns are labeled as a, b, c, . . . , then any pinhole can be represented by index (i,j), where i∈{1, 2, 3, . . . } and j∈{a, b, c, . . . }. Within the needles inserted in the grid locations can be a laser fiber 1 or a thermal sensor 2.

A planning image from a previous patient visit may be used for planning the laser ablation. The laser ablation plan that includes the location and trajectories of laser sources, which are the laser fibers 1 inserted within the needles, ablation zone 6 and the region to be spared (not shown), hereafter referred to as safety zone, is used as the input for the procedure. The plan may be defined such that it corresponds to the grid after the grid has been calibrated to correspond to the frame of reference of the planning image. For example, if a laser source k is to be inserted through a pinhole at location (i,j) to a depth $D_k$, and activated for a duration of $t_k$, then the ablation plan may be completely represented by the set $\{(i,j)_k, D_k, t_k\}$. In addition, locations for insertion of thermal sensors 2 may be planned in advance based on both ablation zones 6 and safety zones. Note that an ablation zone 6 may require application of more than one laser sources 1 simultaneously. Let $T_{safety}^{high}$ and $T_{safety}^{low}$ represent the thresholds for the highest temperature allowed in safety zone beyond which the laser source 1 must be shut down and the maximum temperature threshold before laser source 1 can be activated, respectively. Let $T_{ablation}^{low}$ represent the minimum temperature required in ablation zone 6. In general, $T_{ablation}^{low} > T_{safety}^{high} > T_{safety}^{low}$ and nominal values in tissue for $T_{ablation}^{low}$, $T_{safety}^{high}$ and $T_{safety}^{low}$ are 60° C., 55° C. and 50° C. respectively. Then, the entire laser ablation must be performed such that the temperature in ablation zone reaches higher than $T_{ablation}^{low}$ while the temperature of the safety zone never reaches unsafe limits, i.e., more than $T_{safety}^{high}$.

FIG. 2 shows an overall scheme for a localized targeted laser ablation. The laser source(s) 1 and temperature sensors 2 are placed at the planned locations using a fixed grid 3, which may be attached to an ultrasound transducer or to a guidance tool. The needles may also be directly placed using a guidance tool under live ultrasound guidance. The laser placement is done in two stages: first, a hollow needle, which acts as a guide or sleeve for the laser fiber 1 to be inserted through, is placed to desired location; and then, the laser fiber 1 is inserted along the needle such that the laser source(s) 1 reaches the tip of the needle sleeve. The sleeve may be removed after insertion of the laser fiber. In addition to the laser source(s) 1, needles are also inserted to measure temperatures inside tissue, around the ablation zone 6 and around the safety zone.

The controller 12 acts as an interface between the computer 11 and the hardware through temperature measurements and control of laser delivery. The controller 12 is connected to the output of the thermal sensors 2 and provides the temperature measurements to the computer 11. In addition, controller 12 takes inputs from the computer 11 to start or stop the activation of laser source(s) 1. Alternately, the interface for the temperature sensors 2 may be separate from the laser fiber 1 controller.

The computer 11 executes algorithms for computation and display of thermal maps in addition to the individual thermal sensor 2 measurements as identified on a virtual grid displayed on a monitor. The computer may be, for example, an computing platform having an Intel or AMD quad (or higher) core CPU processor, 16 GB DDR3 memory, a 2 TB hard disk, a 1 TB SSD, and a video controller giving a 256 core GPU. Computations are generally performed by the CPU processor, but some tasks may be performed by the GPU. The computer typically has a gigabit Ethernet port, connected through a switch to a LAN, which in turn is connected to the Internet and/or WAN through a router. Within the LAN or WAN may be a storage network device, or cloud computing resource. As used herein, a "non-transitory" medium is one which stores information in a static or quasi-static physical or electromagnetic state of matter, and which is read out by a sensor which determines the state of the matter. The preferred embodiment of the technology employs non-transitory memories to store data and computer executable instructions, and provides appropriate circuitry to convey the stored information to (and from) the computational hardware.

The user may interact with the computer 11 to define the pinhole locations and laser plan onto the virtual grid. If live ultrasound image is available, the virtual grid is overlaid on the live ultrasound image and the individual needles are defined in at least two orthogonal views containing the needles, which may be presented on different monitors or as portions of the same monitor. The display may show a virtual grid showing a thermal map 13, the laser fibers in the virtual grid 14, isothermal contour showing a safety zone 15, and an isothermal contour showing the ablation zone 16. For a prostate procedure, the two orthogonal views would be transverse, which will correspond with the virtual grid and contain all the pinholes in its place and sagittal, which will contain the entire needle length in its plane. The two views for each needle define the complete placement of needles including locations of laser sources 1. The needles and their grid locations may be manually entered by the user or automatically computed by analyzing the ultrasound video capture after each needle is placed. After all needles and laser sources 1 are placed, the laser ablation may be performed.

Figure 3:
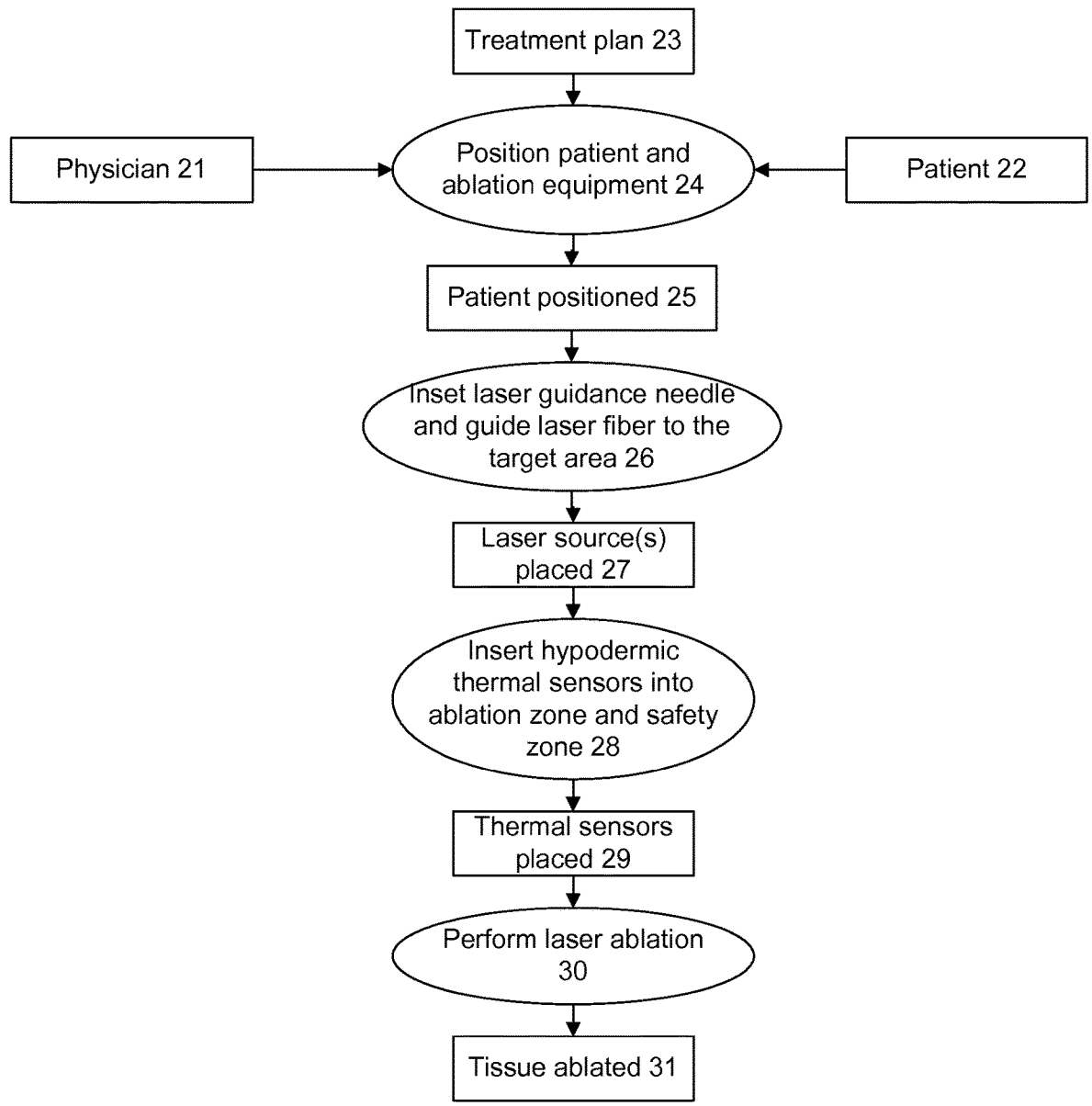
FIG. 3 shows a flowchart of a method for laser ablation using an external grid template and hypodermic needle based thermal sensors.

As shown in FIG. 3, when patient 22 comes for thermal ablation, upon administration of local or general anesthesia, the physician 21 (surgeon) positions the patient 22 and attaches the grid 24 such that the grid locations correspond to the planning image grid points. This may require some physical adjustments based on ultrasound image or some other body markers. For example, for prostate ablation, a transrectal ultrasound transducer may be introduced into the rectum of patient and the grid may be mounted using a rigid fixture on to the probe. The probe pressure and insertion depth then can be adjusted such that the alignment of attached grid template with the virtual template from the planning image is ensured. In another arrangement, external markers or fiducials may be attached on the patient's skin such that they can be used as reference while positioning the ablation equipment relative to a planning image that contains tissue image in addition to the geometry or image of the fiducials. Such a procedure is part of initial calibration before each procedure, which may also include software based co-registration from the planning images to a live imaging modality such as ultrasound. The surgeon defines a treatment plan 23 which includes the order of operations and access to the tissues to be treated.

After positioning the patient 25 and the grid or guidance tool 24 as per the planned procedure, the physician 21 inserts the needles for laser sleeves into place 26 as per the predefined treatment plan 23. As mentioned earlier, this may be done using grid under live ultrasound guidance or ultrasound coupled with a tracking system. When the needles are placed, the physician 21 places the laser fiber 1 by inserting it along the needle sleeve until the tip reaches end of the sleeve. At this point, the sleeve may be withdrawn. Next, the physician 21 inserts the needles containing thermal sensors 28 around the ablation zone and safety zones. Let $T_{safety}$ and $T_{ablation}$ represent the maximum temperature in safety zone and minimum temperature in ablation zone, respectively. The thermal sensors are then placed in position 29, and the laser ablation may proceed 30 according to the plan, resulting in ablated tissue 31.

Figure 4:
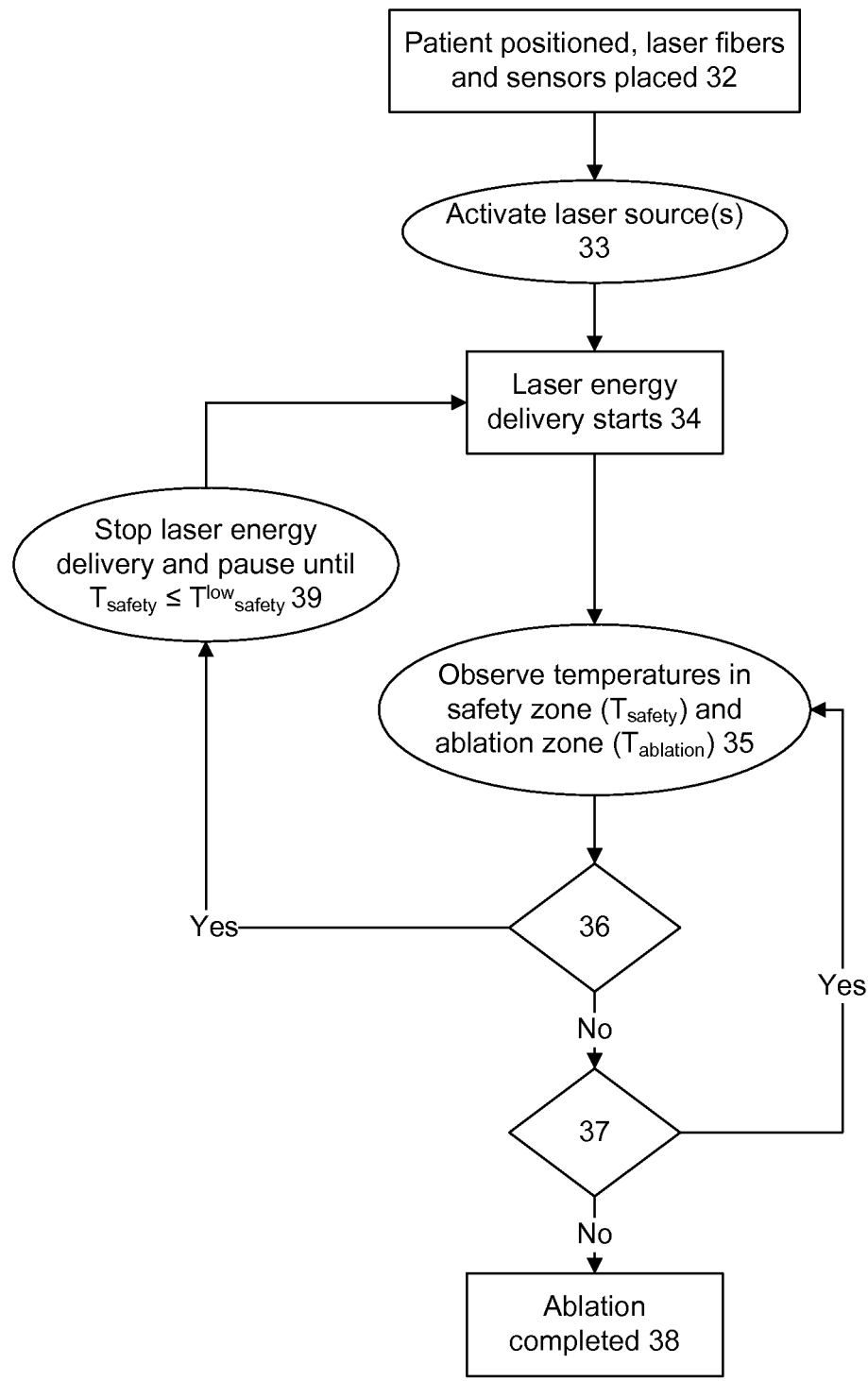
FIG. 4 shows a flowchart of a method for performing laser ablation such that tissue within a safety zone is unharmed while tissue within the ablation zone is completely ablated

FIG. 4 provides a detailed procedure for performing laser ablation while maintaining control of temperatures experienced by ablation and safety zones. Upon placement of the laser source(s) and the thermal sensors 32, the physician 21 activates the laser source(s) 33 and starts delivery of laser energy 34. The computer 11 starts calculating the temperature based on a combination of ultrasound thermometry, heat equations and the measurements at each thermal sensor. The temperatures can be displayed as a color-coded overlay or isothermal contours 15, 16 such that the temperatures in the ablation and safety zones can be computed and monitored in real-time 35. If the safety zone reaches high temperature threshold $T_{safety}^{high}$ before ablation is completed 36, the computer automatically sends signal to controller for shutting off the laser 39. The system then waits for temperature to drop below $T_{safety}^{low}$, following which it activates the laser again 34. The process is repeated until the temperature reaches at least $T_{ablation}^{low}$ inside the ablation zone 37. After the ablation zone is fully treated such that the tissues in that zone have all reached at least $T_{ablation}^{low}$, the ablation is completed 38.

Although certain exemplary embodiments and methods have been described in some detail, for clarity of understanding and by way of example, it will be apparent from the foregoing disclosure to those skilled in the art, that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A system for performing minimally invasive laser ablation of a target tissue within a patient while sparing tissue within a safety zone proximate to the target tissue, comprising:

a guidance tool configured to guide a laser fiber within a patient;

a controller configured to control a laser to deliver energy through the laser fiber;

an invasive thermal sensor and a non-invasive thermal sensor; and at least one automated processor configured to:

measure a temperature within the target tissue using one or more of the invasive thermal sensor and the non-invasive thermal sensor, measure a temperature within the safety zone using one or more of the invasive thermal sensor and the non-invasive thermal sensor, control the controller to deliver a minimally therapeutic ablation therapy to the target tissue based on at least a treatment plan, while ensuring that the safety zone is maintained in a non-ablation condition, compute a thermal profile of the target tissue and the safety zone based on at least a combination of the temperatures measured by the invasive thermal sensor and the non-invasive thermal sensor in conjunction with a real-time tissue image adapted for guidance of the laser fiber with the guidance tool within the patient, generate a thermal map based on the thermal profile, wherein the thermal map illustrates:

the combination of the temperatures measured by the invasive thermal sensor and the non-invasive thermal sensor, an isothermal region representing a highest temperature allowable within the safety zone, and an isothermal region representing a lowest temperature allowable within the target tissue, and cause the thermal map to be overlaid on the real-time ultrasound image.

2. The system according to claim 1, wherein the guidance tool is configured to automatically control insertion of the laser fiber into the patient.

3. The system according to claim 1, wherein the controller is further configured to define a duration and dosage of laser energy delivered through the laser fiber.

4. The system according to claim 1, wherein the non-invasive thermal sensor comprises an ultrasound thermometer.

5. The system according to claim 4, wherein the ultrasound thermometer further generates the real-time image of at least the target tissue during ablation.

6. The system according to claim 1, wherein the at least one automated processor is further configured to communicate with the controller to deactivate the delivery of laser energy through the laser fiber based on the computed thermal profile.

7. The system according to claim 1, wherein the guidance tool is further configured to guide the invasive thermal sensor within the patient.

8. The system according to claim 1, wherein the guidance tool employs at least one of magnetic, optical, mechanical and co-registration software-based tracking.

9. The system according to claim 1, wherein the guidance tool is configured to guide the invasive thermal sensor into the safety zone.

10. The system according to claim 1, wherein the at least one automated processor is further configured to execute software to compute the thermal profile using heat equations, based on at least a duration of application and an energy delivered by the laser fiber, to create the thermal map.

11. The system according to claim 1, wherein the invasive and the non- invasive thermal sensor comprises a combination of a hypodermic thermal sensor, a surface thermal sensor, and an ultrasound signal analysis thermal sensor, which are together analyzed by the at least one automated processor to provide an accurate temperature measurement.

12. The system according to claim 1, wherein the guidance tool comprises a perforated plate having a regular array of holes configured to guide the laser fiber.

13. The system according to claim 1, wherein the guidance tool comprises a perforated plate having a regular array of holes configured to guide the invasive thermal sensor.

14. The system according to claim 1, wherein the guidance tool is mounted to an ultrasonic transducer for generating a real-time ultrasound image, and has an array of guided trajectories which define one at least one plane of a virtual grid and which are configured to guide the laser fiber along a respective guided trajectory.

15. The system according to claim 1, wherein the treatment plan is based on an imaging modality having a first correspondence to a physical coordinate system, and the minimally invasive laser ablation is conducted the real-time tissue image have a second correspondence to the physical coordinate system, the first and second correspondences being different, wherein the at least one automated processor is configured to perform an image transform such that the treatment plan corresponds to the real-time tissue image.

16. The system according to claim 15, wherein the first imaging modality comprises at least one of PET, CT, MM, and MRSI, and the real-time tissue imager comprises an ultrasonic imager.

17. A method for minimally invasive laser ablation of a target tissue within a patient while sparing tissue within a safety zone proximate to the target tissue, comprising:
   guiding a laser fiber within a patient with a guidance tool;
   measuring a temperature within the target tissue using one or more of an invasive thermal sensor and a non-invasive thermal sensor;
   computing a thermal profile of the target tissue and the safety zone based on at least a combination the temperatures measured by the invasive thermal sensor and the non-invasive thermal sensor in conjunction with a real-time tissue image adapted for guidance of the laser fiber with the guidance tool within the patient; and
   controlling a laser to deliver energy through the laser fiber, to deliver a minimally therapeutic ablation therapy to the target tissue while ensuring that the safety zone is continually maintained in a non-ablation condition, based on at least a treatment plan, the measured temperature, and the thermal profile;
   generating a thermal map based on the thermal profile, wherein the thermal map illustrates the combination of the temperatures measured by the invasive thermal sensor and the non-invasive thermal sensor, an isocontour representing a highest temperature allowable within the safety zone, and
   an isocontour representing a lowest temperature allowable within the target tissue; and
   causing the thermal map to be overlaid on the real-time ultrasound image.

18. The method according to claim 17, wherein the guidance tool automatically controls insertion of the laser fiber into the patient.

19. The method according to claim 17, further comprising defining a duration and a dosage of laser energy delivered through the laser fiber.

20. The method according to claim 17, wherein the non-invasive thermal sensor comprises an ultrasound thermometer.

21. The method according to claim 20, wherein the ultrasound thermometer further generates the real-time image of at least the target tissue during ablation.

22. The method according to claim 17, further comprising deactivating the delivery of laser energy through the laser fiber based on at least the computed thermal profile.

23. The method according to claim 17, further comprising guiding the invasive thermal sensor within the patient with the guidance tool.

24. The method according to claim 17, further comprising guiding the invasive thermal sensor within the safety zone with the guidance tool.

25. The method according to claim 17, further comprising computing the thermal profile using heat equations, based on at least a duration of application and an energy delivered by the laser fiber.

26. The method according to claim 17, wherein the invasive and the non- invasive thermal sensor comprises a combination of a hypodermic thermal sensor, a surface thermal sensor, and an ultrasound signal analysis thermal sensor, which are together analyzed to provide an accurate temperature measurement.

27. The method according to claim 17, wherein the guidance tool comprises a perforated plate having a regular array of holes configured to guide the laser fiber and the invasive thermal sensor.

28. The method according to claim 17, wherein the guidance tool is mounted to an ultrasonic transducer for generating a real-time ultrasound image, and has an array of guided trajectories which define at least one plane of a virtual grid and which guide the laser fiber along a respective guided trajectory.

29. The method according to claim 17, wherein the treatment plan is based on an imaging modality having a first correspondence to a physical coordinate system, and the minimally invasive laser ablation is conducted using a second imaging modality have a second correspondence to the physical coordinate system, the first and second correspondences being different, further comprising performing an image transform such that the treatment plan corresponds to an image derived from the second imaging modality.

30. The method according to claim 29 wherein the first imaging modality comprises at least one of PET, CT, MM, and MRSI, and the second imaging modality comprises ultrasound imaging.

31. The method according to claim 17, wherein the target tissue comprises prostate, heart, lung, kidney, liver, bladder, ovaries, thyroid, or brain.

32. The method according to claim 17, wherein the real-time image comprises at least one of a B-mode ultrasound image, two orthogonal planes of ultrasound, and a 3D ultrasound image.

33. The method according to claim 17, wherein the thermal map further comprises an isocontour representing a temperature of the safety zone at which the laser can be reactivated.

34. A non-transitory computer readable medium which stores computer readable instructions to control a programmable processor, for support of minimally invasive laser ablation of a target tissue within a patient while sparing tissue within a safety zone proximate to the target tissue, to perform the steps of:
   receiving data representing at least one temperature within a target tissue and the safety zone based on information from at least one invasive thermal sensor and at least one non-invasive thermal sensor;

computing a thermal profile of the target tissue and the safety zone based on at least a combination of the at least one temperature within a target tissue and the safety zone based on information from the at least one invasive thermal sensor and the at least one non-invasive thermal sensor in conjunction with a real-time tissue image adapted for guidance of a laser fiber toward the target tissue;

controlling a laser to deliver energy through the laser fiber, to deliver a minimally therapeutic ablation therapy to the target tissue while ensuring that the safety zone is continually maintained in a non-ablation condition, based on at least a treatment plan, the measured temperature, and the thermal profile;

generating a thermal map basal on the thermal profile, wherein the thermal map illustrates the combination of the temperatures measured by the invasive thermal sensor and the non-invasive thermal sensor, an isocontour representing a highest temperature allowable within the safety zone, and an isocontour representing a lowest temperature allowable within the target tissue; and causing the thermal map to be overlaid on the real-time ultrasound image.

* * * * *